(12) United States Patent
Ladet

(10) Patent No.: US 9,867,909 B2
(45) Date of Patent: Jan. 16, 2018

(54) MULTILAYER IMPLANTS FOR DELIVERY OF THERAPEUTIC AGENTS

(71) Applicant: Sofradim Production, Trévoux (FR)

(72) Inventor: Sébastien Ladet, Caluire et Cuire (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 14/345,782

(22) PCT Filed: Oct. 1, 2012

(86) PCT No.: PCT/IB2012/002575
§ 371 (c)(1),
(2) Date: Mar. 19, 2014

(87) PCT Pub. No.: WO2013/046057
PCT Pub. Date: Apr. 4, 2013

(65) Prior Publication Data
US 2015/0335795 A1    Nov. 26, 2015

Related U.S. Application Data

(60) Provisional application No. 61/541,533, filed on Sep. 30, 2011.

(51) Int. Cl.
| A61M 31/00 | (2006.01) |
| A61L 31/16 | (2006.01) |
| A61L 31/04 | (2006.01) |
| A61K 9/00  | (2006.01) |
| A61L 31/10 | (2006.01) |
| A61L 17/00 | (2006.01) |
| A61L 17/14 | (2006.01) |

(52) U.S. Cl.
CPC ............ *A61L 31/16* (2013.01); *A61K 9/0024* (2013.01); *A61L 17/005* (2013.01); *A61L 17/145* (2013.01); *A61L 31/042* (2013.01); *A61L 31/10* (2013.01); *A61L 2300/608* (2013.01)

(58) Field of Classification Search
CPC ............................... A61L 31/16; A61L 31/042
USPC ......................................................... 604/93.01
See application file for complete search history.

(56) References Cited

U.S. PATENT DOCUMENTS

| 4,400,833 A | 8/1983 | Kurland |
| 4,511,653 A | 4/1985 | Play et al. |
| 4,931,546 A | 6/1990 | Tardy et al. |

(Continued)

FOREIGN PATENT DOCUMENTS

| EP | 486294 A2 | 5/1992 |
| EP | 0552576 A1 | 7/1993 |

(Continued)

OTHER PUBLICATIONS

International Search Report for PCT/IB12/002575 date of completion is Mar. 6, 2013 (3 pages).

(Continued)

*Primary Examiner* — Kevin C Sirmons
*Assistant Examiner* — Leah Swanson (57) ABSTRACT

Enzymatically degradable compositions containing biocompatible polymers reactive with glycosaminoglycan compositions having a first glycosaminoglycan having a first degree of acetylation and a second glycosaminoglycan having a second degree acetylation different than the first degree of acetylation.

23 Claims, 2 Drawing Sheets

(56) References Cited

U.S. PATENT DOCUMENTS

| | | | |
|---|---|---|---|
| 4,950,483 A | 8/1990 | Ksander et al. |
| 5,201,764 A | 4/1993 | Kelman et al. |
| 5,256,418 A | 10/1993 | Kemp et al. |
| 5,263,983 A | 11/1993 | Yoshizato et al. |
| 5,306,500 A | 4/1994 | Rhee et al. |
| 5,328,955 A | 7/1994 | Rhee et al. |
| 5,350,583 A | 9/1994 | Yoshizato et al. |
| 5,376,375 A | 12/1994 | Rhee et al. |
| 5,399,361 A | 3/1995 | Song et al. |
| 5,413,791 A | 5/1995 | Rhee et al. |
| 5,510,418 A | 4/1996 | Rhee et al. |
| 5,536,656 A | 7/1996 | Kemp et al. |
| 5,565,210 A | 10/1996 | Rosenthal et al. |
| 5,618,551 A | 4/1997 | Tardy et al. |
| 5,681,568 A | 10/1997 | Goldin et al. |
| 5,686,115 A | 11/1997 | Vournakis et al. |
| 5,709,934 A | 1/1998 | Bell et al. |
| 5,766,631 A | 6/1998 | Arnold |
| 5,785,983 A | 7/1998 | Furlan et al. |
| 5,800,541 A | 9/1998 | Rhee et al. |
| 5,861,034 A | 1/1999 | Taira et al. |
| 5,863,984 A | 1/1999 | Doillon et al. |
| 5,871,767 A | 2/1999 | Dionne et al. |
| 5,876,444 A | 3/1999 | Lai |
| 5,962,136 A | 10/1999 | Dewez et al. |
| 5,993,844 A | 11/1999 | Abraham et al. |
| 5,997,895 A | 12/1999 | Narotam et al. |
| 6,083,522 A | 7/2000 | Chu et al. |
| 6,165,488 A | 12/2000 | Tardy et al. |
| 6,197,935 B1 | 3/2001 | Doillon et al. |
| 6,221,109 B1 | 4/2001 | Geistlich et al. |
| 6,264,702 B1 | 7/2001 | Ory et al. |
| 6,312,474 B1 | 11/2001 | Francis et al. |
| 6,391,333 B1 | 5/2002 | Li et al. |
| 6,391,939 B2 | 5/2002 | Tayot et al. |
| 6,410,044 B1 | 6/2002 | Chudzik et al. |
| 6,440,167 B2 | 8/2002 | Shimizu |
| 6,454,787 B1 | 9/2002 | Maddalo et al. |
| 6,500,464 B2 | 12/2002 | Ceres et al. |
| 6,509,031 B1 | 1/2003 | Miller et al. |
| 6,514,286 B1 | 2/2003 | Leatherbury et al. |
| 6,596,304 B1 | 7/2003 | Bayon et al. |
| 6,599,524 B2 | 7/2003 | Li et al. |
| 6,599,690 B1 | 7/2003 | Abraham et al. |
| 6,652,594 B2 | 11/2003 | Francis et al. |
| 6,682,760 B2 | 1/2004 | Noff et al. |
| 6,706,684 B1 | 3/2004 | Bayon et al. |
| 6,730,299 B1 | 5/2004 | Tayot et al. |
| 6,743,435 B2 | 6/2004 | DeVore et al. |
| 6,773,723 B1 | 8/2004 | Spiro et al. |
| 6,790,454 B1 | 9/2004 | Abdul Malak et al. |
| 6,893,653 B2 | 5/2005 | Abraham et al. |
| 6,949,625 B2 | 9/2005 | Tayot |
| 6,974,862 B2 | 12/2005 | Ringeisen et al. |
| 6,977,231 B1 | 12/2005 | Matsuda |
| 7,041,868 B2 | 5/2006 | Greene et al. |
| RE39,172 E | 7/2006 | Bayon et al. |
| 7,098,315 B2 | 8/2006 | Schaufler |
| 7,175,852 B2 | 2/2007 | Simmoteit et al. |
| 7,192,604 B2 | 3/2007 | Brown et al. |
| 7,214,765 B2 | 5/2007 | Ringeisen et al. |
| 7,226,611 B2 | 6/2007 | Yura et al. |
| 7,709,017 B2 | 5/2010 | Tayot |
| 7,718,556 B2 | 5/2010 | Matsuda et al. |
| 7,799,767 B2 | 9/2010 | Lamberti et al. |
| 8,834,864 B2 | 9/2014 | Odar et al. |
| 8,846,060 B2 | 9/2014 | Archibald et al. |
| 8,877,233 B2 | 11/2014 | Obermiller et al. |
| 9,034,357 B2 | 5/2015 | Stopek |
| 2001/0018598 A1* | 8/2001 | Cruise .............. A61B 17/00491 606/214 |
| 2002/0042473 A1* | 4/2002 | Trollsas ................ A61L 24/043 525/54.1 |
| 2003/0114937 A1 | 6/2003 | Leatherbury et al. |
| 2003/0129730 A1 | 7/2003 | Chenite et al. |
| 2003/0133967 A1 | 7/2003 | Ruszczak et al. |
| 2004/0059356 A1 | 3/2004 | Gingras |
| 2004/0101546 A1 | 5/2004 | Gorman et al. |
| 2004/0215231 A1 | 10/2004 | Fortune et al. |
| 2005/0002893 A1 | 1/2005 | Goldmann |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2008/0317813 A1* | 12/2008 | Craig ...................... A61L 31/10 424/423 |
| 2009/0004276 A1* | 1/2009 | Ben-Shalom ........... A23L 1/056 514/1.1 |
| 2009/0068250 A1* | 3/2009 | Gravagna ............... A61L 27/24 424/426 |
| 2009/0269479 A1* | 10/2009 | Pacetti .................... A61L 31/10 427/2.24 |

FOREIGN PATENT DOCUMENTS

| | | | | |
|---|---|---|---|---|
| EP | 0625891 B1 | 11/1994 | | |
| EP | 1017415 B1 | 7/2000 | | |
| EP | 0693523 B1 | 11/2002 | | |
| EP | 1315468 B1 | 6/2003 | | |
| EP | 1384774 A1 | 1/2004 | | |
| EP | 1484070 B1 | 12/2004 | | |
| EP | 1561480 A2 | 8/2005 | | |
| EP | 1782848 A2 | 5/2007 | | |
| FR | 2715405 A1 | 7/1995 | | |
| JP | 2000502380 A | 2/2000 | | |
| JP | 2004507472 A | 3/2004 | | |
| JP | 2011500955 A | 1/2011 | | |
| WO | 9831345 A1 | 7/1998 | | |
| WO | WO 02/17853 A2 | 3/2002 | | |
| WO | 03002168 A1 | 1/2003 | | |
| WO | 2004078120 A2 | 9/2004 | | |
| WO | 2005112820 A2 | 12/2005 | | |
| WO | 2007048099 A2 | 4/2007 | | |
| WO | WO 2010/043978 A2 | 4/2010 | | |
| WO | WO 2010/043979 A2 | 4/2010 | | |
| WO | WO 2010043980 A2 * | 4/2010 | ............. A61L 27/48 |
| WO | 2010095044 A2 | 8/2010 | | |
| WO | WO 2011/117758 A2 | 9/2011 | | |
| WO | WO 2012127328 A1 * | 9/2012 | ............. C08J 3/075 |

OTHER PUBLICATIONS

CN Office Action dated Feb. 24, 2016 in corresponding CN Patent Application No. 201280048332.6, together with English-language translation, 13 pages.

European Search Report corresponding to European Application No. EP 12 19 4841.8, completed on Jun. 12, 2013 and dated Jun. 19, 2013; 5 pages.

Freier, T. et al., "Controlling Cell Adhesion and Degradation of Chitosan Films by N-acetylation," Biomaterials, Apr. 9, 2005, pp. 5872-5878, vol. 26.

Collins, R., et al., "Use of Collagen Film as a Dural Substitute: Preliminary Animal Studies," Journal of Biomedical Materials Research, Feb. 1991, pp. 267-276, vol. 25, Issue 2.

Sorlier P. et al., "Relation Between Solution Properties and Degree of Acetylation of Chitosan: Role of Aging," Biomacromolecules, Oct. 2002, pp. 1336-1342, vol. 3.

International Search Report corresponding to International Application No. PCT/IB2008/003107, completed on Feb. 26, 2010 and dated Mar. 8, 2010; 3 pages.

Australian Examination Report dated Jul. 13, 2016 in corresponding Australian Patent Application No. 2012313983, 2 pages.

European Office Action corresponding to EP 12808468.8 dated Aug. 25, 2015.

(56) References Cited

OTHER PUBLICATIONS

Aiba, S., "Studies on Chitosan, Reactivity of Partially N-acetylated Chitosan in Aqueous Media," Makromol. Chem., Jan. 1993, pp. 65-75, vol. 194.

Japanese Office Action dated Sep. 13, 2016 in corresponding Japanese Patent Application No. 2014-532502, together with English translation, 6 pages.

Chinese Office Action dated Sep. 13, 2016 in corresponding Chinese Patent Application No. 201280048332.6 together with English translation, 16 pages.

Japanese Office Action dated May 9, 2016 in corresponding Japanese Patent Application No. 2014-532502, together with English translation, 7 pages.

* cited by examiner

FIG. 5

MULTILAYER IMPLANTS FOR DELIVERY OF THERAPEUTIC AGENTS

CROSS-REFERENCE TO RELATED APPLICATIONS

This application is a National Stage Application of PCT/IB2012/002575 under 35USC §371 (a), which claims benefit of and priority to U.S. Provisional Patent Application Ser. No. 61/541,533 filed Sep. 30, 2011, the disclosures of each of the above-identified applications are hereby incorporated by reference in their entirety.

BACKGROUND

Technical Field

The present disclosure relates to multilayer implants, and more particularly, multilayer implants suitable for delivering therapeutic agents including a first layer comprising at least one glycosaminoglycan having a first degree of acetylation and a second layer comprising at least one glycosaminoglycan having a degree of acetylation different from the first degree of acetylation.

Background of Related Art

Delivery of a therapeutic agent through the use of implantable medical devices is described in a wide variety of manners. Existing methods of such delivery of a therapeutic agent predominantly focus on the use of water-soluble drugs and polymers to form thin surface coatings positioned on the surface of the medical device which provide limited therapeutic payload and limited control over the release of the therapeutic agent.

In addition, highly water-soluble drugs may be difficult to formulate for controlled or sustained release in that highly water-soluble drugs may either: be susceptible to hydrolysis and quickly released in an aqueous environment thereby being unable to maintain a controlled or sustained release, or, offer limited solubility in the organic systems particularly useful with hydrophobic or water-insoluble drug carriers, i.e., hydrophobic polymers. Limited solubility of the highly water-soluble drugs may further lead to poor encapsulation efficiencies of the drug and limited therapeutic payload on the implantable device. Such hydrophilic drugs need a sufficient water barrier to sustain release. Current systems are challenged from a drug payload and sustained release standpoint including offering therapeutic benefits.

Poly(ethylene glycol) (PEG), a hydrophilic polymer that exhibits acceptable toxicity, and immunogenicity has found great utility in biotechnology, specifically, in forming films, foams and/or hydrogels. PEG is generally considered to be biocompatible and is not immunogenic, which is to say that PEG is generally capable of coexistence with living tissues and does not tend to produce an immune response in the body. However, conventional films, foams, or hydrogels and other medical implants based on PEG and other synthetic biocompatible polymers may be susceptible to in-vivo degradation, generally induced by hydrolysis of specific linkages of the polymer chains (e.g., ester linkages). Thus, such degradation profiles may be considered passive, since degradation primarily occurs due to the presence of water. It would be desirable to provide implants which may include PEG, PEG derivatives, or other synthetic biocompatible polymers that may be suitable for in-vivo enzymatic degradation. It would be beneficial to provide implantable medical devices capable of controlling the release of a therapeutic agent by including tunable or controllable materials via enzymatic degradation and which are not limited by their susceptibility to hydrolysis only.

SUMMARY

The present disclosure describes multilayer implants suitable for delivery of at least one therapeutic agent. In embodiments, the implants include a first layer containing a first glycosaminoglycan composition including at least one first glycosaminoglycan having a first degree of acetylation, and a second layer which contains a second glycosaminoglycan composition including at least one second glycosaminoglycan having a second degree acetylation different than the first degree of acetylation. The implants may further include at least one therapeutic agent in at least one of the layers.

In embodiments, the multilayer implants for delivery of a therapeutic agent include a first layer containing a first glycosaminoglycan composition which includes a first glycosaminoglycan having a first degree of acetylation and a second glycosaminoglycan having a second degree acetylation different than the first degree of acetylation, and a second layer containing a second glycosaminoglycan composition which includes a third glycosaminoglycan having a third degree acetylation and a fourth glycosaminoglycan having a fourth degree acetylation different than the third degree of acetylation. At least one of the first and second layers further includes a therapeutic agent.

In embodiments, the first glycosaminoglycan composition comprises a glycosaminoglycan selected from the group consisting of hyaluronic acid, chondroitin, dermatan, chitin, chitosan, keratan, heparin, and derivatives and combinations thereof. In embodiments, the second glycosaminoglycan composition comprises a glycosaminoglycan selected from the group consisting of hyaluronic acid, chondroitin, dermatan, chitin, chitosan, keratan, heparin, and derivatives and combinations thereof.

In embodiments, the first and second glycosaminoglycan compositions comprise the same glycosaminoglycan. Alternatively, the first and second glycosaminoglycan compositions may comprise different glycosaminoglycan.

In embodiments, the first glycosaminoglycan comprises a degree of acetylation of about 1% to about 10%. In embodiments, the second glycosaminoglycan comprises a degree of acetylation of about 10% to about 70%.

In certain embodiments, a multilayer implant suitable for delivery of a therapeutic agent is described which includes a first layer containing a first chitosan composition bonded to a first biocompatible polymer including pendant electrophilic groups. The first chitosan composition includes at least one first chitosan having a first degree of acetylation. The implant also includes a second layer containing a second chitosan composition bonded to a second biocompatible polymer including pendant electrophilic groups, the second chitosan composition including at least one second chitosan having a second degree acetylation different than the first degree of acetylation. At least one of the first and second layers further includes a therapeutic agent. A therapeutic agent may be combined or linked to any layer and/or any portion of the layer.

In embodiments, the biocompatible polymer comprises a poly(ethylene glycol) functionalized to include pendant electrophilic groups. In embodiments, the biocompatible polymer comprises electrophilic groups selected from the group consisting of N-hydroxysuccinimide ester (NHS), N-hydroxysulfosuccinimide ester (SNHS), N-hydroxyethoxylated succinimide ester (ENHS) and combinations thereof. In embodiments, the first chitosan comprises a degree of acetylation of about 1% to about 10%. In embodiments, the second chitosan comprises a degree of acetylation of about 10% to about 70%.

In embodiments, the therapeutic agent is selected from the group consisting of antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, enzymes and combinations thereof. For example, the therapeutic agent comprises an antimicrobial agent.

In embodiments, the implant further comprises a mesh.

In other embodiments, methods of making the multilayer implants are also described herein.

BRIEF DESCRIPTION OF THE DRAWINGS

The present disclosure will be more clearly understood from the following description in connection with the accompanying drawings in which.

DETAILED DESCRIPTION

The present disclosure describes multilayer implants suitable for delivery of at least one therapeutic agent. The multilayer implants include at least a first and second layer. The multilayer implants also include at least one glycosaminoglycan having a first degree of acetylation and at least one glycosaminoglycan having a second degree of acetylation different than the first degree of acetylation and a therapeutic agent included in some portion of the implant.

It is envisioned that the multilayer implants described herein may include any number of layers and/or configurations of layers. For example, in embodiments the implants may include only two layers of the same dimension and/or thickness. In another example, in embodiments the implants may include three layers wherein at least one of the layers vary in thickness and/or dimension from the other layers.

It is further envisioned that the multilayer implants described herein may include any number and/or combination of glycosaminoglycans having different degrees of acetylation, in a single layer and/or in any combination of layers. For example, in embodiments the implants may include a single layer which includes at least two glycosaminoglycans having different degrees of acetylation. In other examples, in embodiments the implants may include a first layer which includes multiple glycosaminoglycans wherein at least one of the glycosaminoglycans has a different degree of acetylation and a second layer which includes at least one glycosaminoglycan having a different degree of acetylation from at least one of the glycosaminoglycans of the first layer in this embodiment.

The glycosaminoglycan compositions may include any combination of various glycosaminoglycans having different degrees of acetylation. Glycosaminoglycans are long-branched polysaccharides which contain repeating disaccharide units having various amounts of pendant acetylated amines. Depending upon the degree of acetylation, some portion of the pendant amines will not be acetylated, leaving that portion reactive with electrophilic groups on other surrounding materials or compounds, such as a biocompatible polymer included in the implant, a therapeutic agent, and/or natural materials found in tissue near the site of implantation.

Any suitable glycosaminoglycan having free amine groups may used to form the compositions described herein. In embodiments, the free amine groups may interact with the electrophilic groups of a biocompatible polymer included in the implant to form a covalent bond or cross-link. Some non-limiting examples of suitable glycosaminoglycans include hyaluronic acid, chondroitin, dermatan, chitin, chitosan, keratan, heparin, and derivatives and combinations thereof. In some embodiments, the glycosaminoglycan composition may include two or more of the same glycosaminoglycans wherein the glycosaminoglycans include different varying degrees of acetylation. For example, in some embodiments, the glycosaminoglycan composition includes at least two chitosan compounds of varying degrees of acetylation.

Chitosan is a natural linear co-polymer of N-acetyl D-glucosamine (acetylated unit) and D-glucosamine (non-acetylated unit). Chitosan may be produced by partial or full deacetylation of chitin. Chitin may be extracted from natural sources, e.g., squid pens, exoskeletons of crustaceans such as shrimp shells, or vegetable sources such as mushrooms, e.g. "champignon de Paris." Chitosan may also be synthetically produced or synthesized by modified microorganisms such as bacteria.

The structure of native chitosan provides viscoelastic properties as well as specific interactions with biological substrates that may not be found in other modified polysaccharides, such as polysaccharides in which the —$NH_2$ group would be chemically added. Chitosan, then, may provide excellent viscosity for forming films, foams and/or gels which also may be biologically accepted.

The adhesion of chitosan with other polymers includes the association of different kinds of interactions, such as electrostatic interactions, hydrogen bonds, and hydrophobic interactions, to name a few. Chitosan, under certain circumstances, is a cationic polymer containing $NH_3^+$ groups. The positively charged primary amino groups of chitosan attract anionic groups of other polymers. Thus, chitosan and anionic polymers are able to form polyelectrolyte complexes. Polyelectrolyte complex formation may improve the mechanical properties of the polymers and lead to new structures, such as precipitates, films, foams, fibers, and gels.

Adhesion of chitosan with other polymers may also be promoted by reinforcing the mechanical properties of the formulation by creating covalent bonds between both the components of the each layer and/or between the components of different layers of the multilayer implant. Chitosan has $NH_2$ groups which can react covalently with pendant electrophilic groups of any implantable material.

The degree of acetylation (DA), or the percentage of N-acetyl D-glucosamine, in the glycosaminoglycans may be from about 0% to about 90%. In embodiments, the degree of acetylation may be from about 0% to about 50%. In embodiments, the degree of acetylation may be from about 0% to about 10%. Although described in a variety of ranges, the differences in degree of acetylation of any two glycosaminoglycans may be as little as about 2% and as much as about 90% and includes any number individually positioned therebetween.

The degree of acetylation in the glycosaminoglycans may affect the in vivo persistence and/or degradation time of the glycosaminoglycan compositions described herein. For example, glycosaminoglycans displaying a low DA, i.e., 0% to 20% may display a shorter in vivo persistence than glycosaminoglycans having a high DA, i.e., 70% to 90%. In embodiments, immediate, sustained and/or controlled release of a therapeutic agent from the implants described herein may be controlled using multiple layers of varying degrees of acetylation and varying in vivo persistence.

Low DA's also ensure that sufficient amounts of $NH_3^+$ are available to generate ionic interactions. Low DA's also ensure that the glycosaminoglycan has the capability, (e.g., free amino groups), to be crosslinked with a functionalized synthetic polymer. The glycosaminoglycan may have a molecular weight from about 1,000 g/mol to about 1,000,000 g/mol. In embodiments, glycosaminoglycan a molecular weight of about 2,000 g/mol to about 900,000 g/mol.

Methods for controlling the degree of acetylation are known in the art, and any suitable method may be used to tune and/or control the degree of acetylation of the glycosaminoglycans. For example, the treatment of the glycosaminoglycan with sodium or potassium hydroxide is one way to control the acetylation of glycosaminoglycans. By varying the temperature, concentration of the hydroxide, and/or the pH, one skilled in the art can control the level at which the degree of acetylation may be altered. The degree of acetylation can be also obtained after a reaction of reacetylation using for example anhydric acetic as an acetylation chemical reactant.

The glycosaminoglycan compositions may include a mixture of glycosaminoglycans in any physical form. In some embodiments, the glycosaminoglycan composition may be in a dry particulate form, i.e., a powder or granule. In other embodiments, the glycosaminoglycan composition may be a solution. For example, a solution of two chitosan compounds having different degrees of acetylation may be prepared by dissolving the two chitosan compounds in distilled water with a stoechiometric amount of HCl to ensure the complete protonation of all $NH_2$ groups. The final solution may contain about 0.5% (w/w) to about 20% (w/w) chitosan.

In embodiments, the individual layers of the multilayer implants described herein may be a film, foam, gel and combinations thereof. For example, a first glycosaminoglycan solution including at least one glycosaminoglycan and a therapeutic agent may be extruded to form a first layer film and a second glycosaminoglycan solution including a glycosaminoglycan having a different degree of acetylation from the first solution may be lyophilized or freeze-dried to form a second layer foam. By placing the second layer foam in contact with the first layer film prior to drying of the film, the foam may attach to the at least slightly wet film to form a multilayer implant. In embodiments, the addition of a suitable adhesive or any additional securement means, i.e., staples, stitches, and the like, may also be used to securely attach the foam to the film.

In the art, there may be suitable methods for forming the glycosaminoglycans into films, foams or gels. For example, film-forming processes may include extrusion, molding, injection molding, solvent casting, ultrasonic spraying, and the like. In another example, foam-forming processes include freeze-drying, lyophilization, and the like. Any single and/or combination of these suitable processes may be used to form the multilayer implants described herein.

In embodiments, the glycosaminoglycan composition may include two different chitosan compounds having different degrees of acetylation. The first chitosan compound may have a relatively low DA, which may be from about 0% to about 10%, in embodiments from about 1% to about 2%. The second chitosan compound may have a higher DA than the DA of the first chitosan compound. The DA of the second chitosan compound may be from about 10% to about 80%, in embodiments, from about 15% to about 70%. The chitosan content of the glycosaminoglycan composition may include: a) from about 70% to about 100% of the first chitosan compound, in embodiments, from about 80% to about 95% of the first chitosan compound; and b) from about 0% to about 30% of the second chitosan compound, in embodiments, from about 5% to about 20% of the second chitosan compound. Without being bound any particular theory, it is believed that the combination of low and high DA chitosan compounds modifies the balance between hydrophilic and hydrophobic interactions of the chitosan content of the composition, which may be useful when combined with hydrophilic and/or hydrophobic therapeutic agents.

The implants described herein may further include at least one biocompatible polymer in combination with glycosaminoglycans having different degrees of acetylation. The combination of the polymer and the glycosaminoglycans may form layers susceptible to hydrolysis and/or enzymatic degradation. In some embodiments, the combination of glycosaminoglycans having different degrees of acetylation are susceptible to varying degrees of enzymatic degradation. In some embodiments, the biocompatible polymers are susceptible to hydrolysis.

The biocompatible polymers described herein may be natural or synthetic and include electrophilic reactive groups capable of interacting with the free amino groups found in the combination of glycosaminoglycans of varying degrees of acetylation to form bonds. In certain embodiments, the glycosaminoglycans may be combined with at least one synthetic biocompatible polymer having pendant electrophilic groups.

Synthetic biocompatible polymer includes any oligomer or polymer that is not naturally occurring and/or is produced via chemical synthesis or modification. Examples of suitable synthetic biocompatible polymers may include any biocompatible polymer which has been chemically modified to include electrophilic reactive groups and derivatives of such polymers. In addition, natural biopolymers which have been modified, such as to include degradable linkages, and/or functionalized to include electrophilic reactive groups may also be suitable examples of synthetic biocompatible polymers.

The biocompatible polymers may be absorbable, non-absorbable, hydrophilic, hydrophobic and combinations thereof. The biocompatible polymers may also be linear, branched, star-shaped, dendrimetic and the like. In embodiments, the synthetic biocompatible polymer is poly(ethylene glycol) or a derivative of poly(ethylene glycol).

Poly(ethylene glycol) and derivatives thereof in accordance with the present disclosure are capable of reacting with the glycosaminoglycan compositions to form a bond therewith. The PEG derivatives described herein may be functionalized or activated PEG derivates that are substantially non-toxic and should not produce undesirable effects.

As used herein the terms "group," "functional group," and/or "reactive group," may all be somewhat synonymous in the chemical arts and may be used in the art and herein to refer to distinct, definable portions or units of a molecule or polymer and to units that perform some function or activity and may be reactive with other molecules or polymers.

As used herein the term "linkage" is used to refer to groups that may be formed as the result of a chemical reaction and typically may be covalent linkages. Hydrolytically stable linkages mean that the linkages may be stable in water and do not react with water at useful pHs for an extended period of time, potentially indefinitely. Hydrolytically unstable linkages may be those that react with water, typically causing a molecule to separate into two or more components. A linkage is said to be hydrolysable if the linkage is susceptible to hydrolysis.

In embodiments, any of the glycosaminoglycans described herein may be combined with a functionalized or activated synthetic biocompatible polymer having at least one electrophilic group to form at least one layer of the multilayer implants. For example, in some embodiments, a chitosan composition including a first chitosan compound having a first degree of acetylation and a second chitosan compound having a second degree acetylation higher than the first degree of acetylation may be combined with a functionalized or activated synthetic biocompatible polymer having at least one electrophilic group to form various compositions, such as films, foams, hydrogels and the like. The ratio of the chitosan composition to the synthetic biocompatible polymer may be adjusted to provide a desired formulation. Each formulation is characterized by its mix ratio (MR). As used herein, the term "mix ratio" means the amount of free amine groups of chitosan over the amount of electrophilic groups of the functionalized synthetic biocompatible polymer. The mix ratio may be at least about 1, in embodiments from about 1 to about 40. Further, the chitosan content of the chitosan composition may be adjusted to achieve a desired strength and/or degradation profile of the resulting adhesive. In other words, adjusting the total degree of acetylation by combining two or more chitosan compounds having different degrees of acetylation provides for fine tuning of the degradation profile of the resulting composition.

Even though the interaction between the glycosaminoglycans and the synthetic biocompatible polymers may be due to covalent bonding, the importance of physical gelation due to the behavior of the glycosaminoglycan under physiological conditions cannot be neglected. For example, interactions between chitosan and other functionalized biopolymers, such as oxidized starch, have been studied by FTIR, NMR, and rheology. Covalent bonds exist between the two polymers, but it may coexist with other types of interactions such as hydrogen bonding or hydrophobic interactions.

In embodiments, the synthetic biocompatible polymers according to the present disclosure include at least two pendant electrophilic functional groups capable of reacting with free amine groups on the first and/or second glycosaminoglycans. The synthetic biocompatible polymers may include a multifunctional core, with one more than one arms each having a pendant or terminal electrophilic functional group capable of reacting with the free amines on the first and/or second glycosaminoglycans. It should be understood that only one arm may be attached to the core which includes a terminal functional group capable of reacting with an amine group, with no other groups attached to the core or with non-reactive arms attached to the core. The other arms may be, for example, simple —OH terminated PEG arms or PEG-based arms terminated with reactive groups that are not amine-reactive. In embodiments, the present synthetic biocompatible polymers may include anywhere from 1 to 8 arms that include a terminal functional group capable of reacting with an amine group on the first and second glycosaminoglycans.

The functional group may be an electrophilic functional group. Some examples of electrophilic groups capable of reacting with the glycosaminoglycan compositions include, but are not limited to, N-hydroxysuccinimide ester (NHS), N-hydroxysulfosuccinimide ester (SNHS), and N-hydroxyethoxylated succinimide ester (ENHS).

The advantage of the NHS-amine reaction may be that the reaction kinetics leads to quick gelation usually within about 10 minutes, in embodiments from about 10 seconds to about 1 minute. This fast gelation is particularly useful for in situ reactions on live tissue. The NHS-amine crosslinking reaction leads to formation of N-hydroxysuccinimide as a side product. The sulfonated or ethoxylated forms of N-hydroxysuccinimide may be useful due to their increased solubility in water and hence their rapid clearance from the body. The sulfonic acid salt on the succinimide ring does not alter the reactivity of NHS group with the primary amines.

A biocompatible polymer functionalized to include pendant electrophilic groups, such as a multi-arm poly(ethylene glycol) including pendant -NHS groups, may be combined with a glycosaminoglycan composition containing free amine groups to form a crosslinked polymer. In embodiments, the glycosaminoglycan composition includes more than one amine group and essentially serves as a crosslinker. Generally, any combination of glycosaminoglycans having free amine groups may be used to form a glycosaminoglycan composition suitable for interacting with the synthetic biocompatible polymers described herein.

The resulting crosslinked polymer may include hydrolysable and non-hydrolysable portions. More specifically, the resulting film, foam, or hydrogel may contain hydrolysable portions found in the biocompatible polymer which may be susceptible to passive degradation by the exposure of aqueous fluids and potentially resulting in a faster or initial release of a therapeutic agent. The resulting film, foam, or hydrogel may also contain non-hydrolysable portions in the glycosaminoglycan portions which may be susceptible to a less passive and/or more controllable degradation process such as enzymatic degradation, wherein the varying degrees of acetylation of the multiple glycosaminoglycans may be varied to increase or decrease the hydrogel or polymers degradation time (also known as the in-vivo persistence) and potentially result in a slower sustained or controlled release of the therapeutic agent from the implant.

In terms of degradation of the resulting synthetic biocompatible polymer/glycosaminoglycan composition film, foam or hydrogel, while not wishing to be bound by any theory, it is believed that the varying degrees of acetylation of the glycosaminoglycans provides the hydrogel or polymer with varying degrees of in-vivo persistence. As a result, the in-vivo persistence of the resulting crosslinked polymers may be dependent upon or controlled by the degree of acetylation of the glycosaminoglycans.

As noted above, the synthetic biocompatible polymer, i.e., a PEG derivative, may include multiple arms wherein each arm includes a pendant NHS group which may be reactive with a glycosaminoglycan composition having varying degrees of acetylation. In embodiments, the combination of the number of pendant NHS groups in the biocompatible polymer and the number of pendant amine groups in the glycosaminoglycan composition may total greater than or equal to 5 to form a cross-linkable hydrogel. A glycosaminoglycan composition including two or more glycosaminoglycans which includes at least 2 or more pendant amine groups may be combined with a multi-arm biocompatible polymer having at least two arms to form a cross-linked materials suitable for use as a scaffold, adhesion barrier, therapeutic delivery device, tissue-support, tissue-filler and the like. Of course, any combination of pendant NHS and amines totaling 5 or more may be suitable for forming suitable cross-linked polymers or hydrogels.

The synthetic biocompatible polymers, i.e., degradable poly(ethylene glycol) derivatives, described herein may be combined with a glycosaminoglycan composition to form any layer of the multilayer implant described herein. In addition, the multilayer implants may be combined with any suitable medical device including, but not limited to, a stent, mesh, suture, staple, balloon, suture anchor, bone plate, pin, screw, rod, and the like.

In embodiments, several biocompatible crosslinked materials may be produced using the synthetic biocompatible polymers and glycosaminoglycan compositions described herein. The reaction conditions for crosslinking will depend on the nature of the functional groups. In embodiments, the reactions may be conducted in buffered aqueous solutions at pH 5 to 12. Suitable non-limiting examples of buffers may include sodium borate, triethanol amine, sodium phosphate, carbonate, and potassium hydrogen phthalate. Elevated pH may increase the speed of the reactions. In some embodiments, organic solvents such as ethanol or isopropanol may be added to improve the reaction speed or to adjust the viscosity of a given formulation.

Without being bound by any theory, it is believed the crosslinked films, foams, or gel described above degrade due to hydrolysis of the ester linkage in the biocompatible polymer and enzymatic degradation of the inner amide bond in the acetylated glycosaminoglycan. Aqueous solutions of the synthetic biocompatible polymers and glycosaminoglycan compositions described herein may be made just before the crosslinking reaction due to reaction of NHS groups with water. Longer "pot life" may be obtained by keeping these solutions at lower pH (e.g., from about 4 pH to about 5 pH).

The crosslinking density of the resultant biocompatible crosslinked polymer may be controlled by the overall molecular weight of the synthetic biocompatible polymers and glycosaminoglycan compositions and the number of functional groups available per molecule. A lower molecular weight between crosslinks such as 600 will give much higher crosslinking density as compared to a higher molecular weight such as 10,000. In embodiments, higher molecular weight synthetic biocompatible polymers may be used. In some embodiments, synthetic biocompatible polymers of more than 3000 may be used so as to obtain elastic gels.

In embodiments, at least one therapeutic agent may be included in the implants described herein. The agents may be freely admixed with the components of any layer of the multilayer implant or may be tethered to the components through any variety of chemical bonds. In these embodiments, the multilayer implants serve as a vehicle for delivery of the agent. The term "therapeutic agent" as used herein, is used in its broadest sense and includes any substance or mixture of substances that have clinical use. Consequently, therapeutic agents may or may not have pharmacological activity per se, e.g., a dye, or fragrance. Alternatively a therapeutic agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the therapeutic agent may be added to the glycosaminoglycan compositions in any suitable form of matter, e.g., powders, liquids, gels, and the like.

Examples of classes of therapeutic agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of therapeutic agents may be used.

Other therapeutic agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable therapeutic agents include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factors, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Therapeutic agents can also be additives, such as fucans, emulsifiers, surfactants, humectants, buffering agents, pH modulators, chelating agents, viscosity agents, and any other product which may enhance tissue repair, limit the risk of sepsis, and modulate mechanical properties of the degradable compositions. It is envisioned that metal ions known for their bioactivity in favor of tissue regeneration may also be used.

Figure 1:
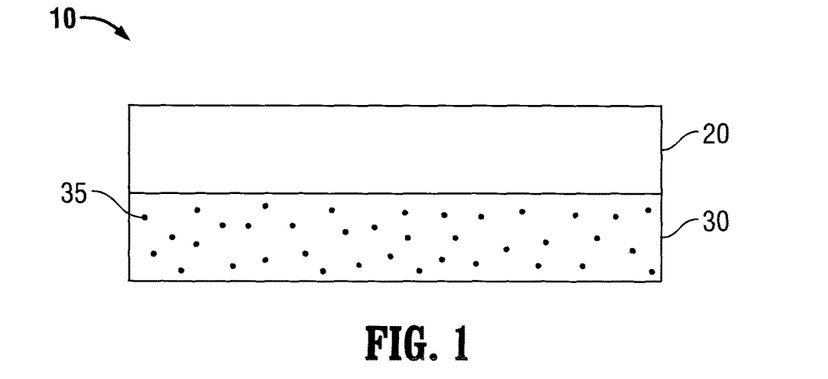
FIG. 1 is a side view of a multilayer implant according to at least one embodiment described herein.

Turning now to FIG. 1, multilayer implant 10 is shown including first layer 20 which includes at least one glycosaminoglycan having a first degree of acetylation and second layer 30 which includes at least one glycosaminoglycan having a second degree of acetylation different than the first degree of acetylation. Therapeutic agent 35 is shown incorporated into second layer 30. It is envisioned that upon degradation of second layer 30 via hydrolytic and/or enzymatic degradation, therapeutic agent 35 may be released from multilayer implant 10.

Figure 2:
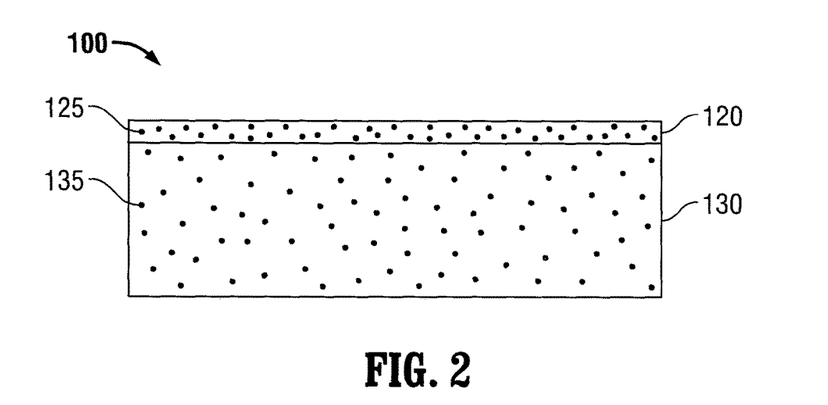
FIG. 2 is side view of a multilayer implant according to at least one embodiment described herein.

In embodiments, as shown in FIG. 2, multilayer implant 100 may include first film layer 120 containing a glycosaminoglycan composition having a first glycosaminoglycan having a first degree of acetylation and a second glycosaminoglycan having a second degree of acetylation different from the first glycosaminoglycan. First therapeutic agent 125 is incorporated into first layer 120. Second foam layer 130 contains a second glycosaminoglycan composition having a third glycosaminoglycan having a third degree of acetylation and a fourth glycosaminoglycan having a fourth degree of acetylation different from the third glycosaminoglycan. Second therapeutic agent 135 is incorporated into second layer 130. In embodiments, first film layer 120 may act as an adhesion barrier and include an anti-adhesive agent as first therapeutic agent 125. In embodiments, second foam layer 130 may act as scaffold for cellular attachment and/or tissue ingrowth and may include at least one second therapeutic agent 135 suitable for promoting attachment or ingrowth, such as growth hormones, growth factors, enzymes, clotting agents, adhesives and the like.

Figure 3:
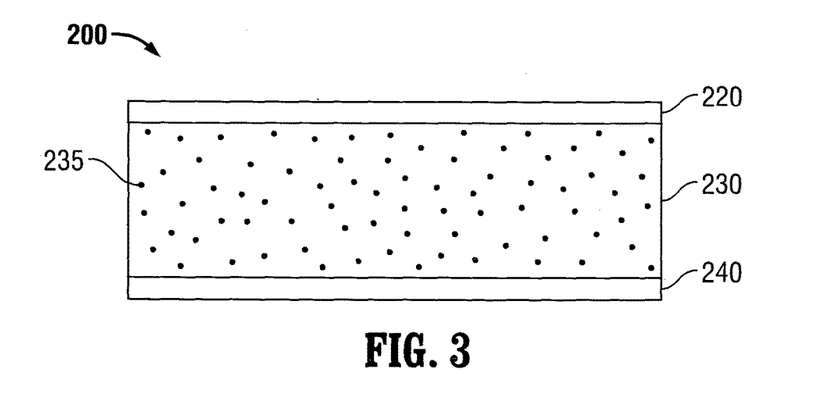
FIG. 3 is side view of a multilayer implant according to at least one embodiment described herein.

In still other embodiments, the multilayer implants described herein may include more than two layers. For instance, as shown in FIG. 3, first layer 230 includes at least one glycosaminoglycan having a first degree of acetylation and is sandwiched between second layer 220 and third layer 240. At least one of second layer 220 and third layer 240 including which a second glycosaminoglycan having a second degree of acetylation different from first layer 230. In embodiments, the degree of acetylation of the glycosaminoglycan(s) in second layer 220 and/or third layer 240 are higher or lower than the first degree of acetylation of the glycosaminoglycan in first layer 230. In such embodiments, the degradation of second layer 220 and third layer 240 will slow down the degradation of first layer 230 and the release of therapeutic agent 235 incorporated in first layer 230.

Although the multilayer implants described herein include sufficient tensile strength to be utilized independent of other medical devices, in some embodiments, the multilayer implants may be combined with other suitable medical devices, such as for instance a surgical staple, screw, pin, suture, surgical mesh or other fibrous reinforcement member. In embodiments, porous reinforcement member, such as a surgical mesh, may further enhance the multilayer implants ability to promote cellular attachment and/or tissue ingrowth into the implant.

Figure 4:
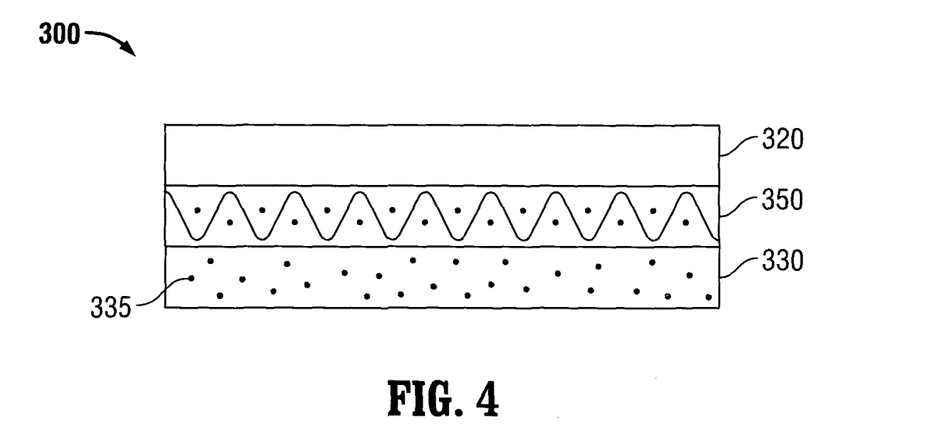
FIG. 4 is side view of a multilayer implant according to at least one embodiment described herein.

As illustrated in FIG. 4, multilayer implant 300 includes surgical mesh 350 positioned between first layer 320 and second layer 330. First layer 320 includes at least a first glycosaminoglycan, i.e., chitosan, having a first degree of acetylation and second layer 330 includes at least one second glycosaminoglycan, i.e., chitosan, having a second degree of acetylation different from the degree of acetylation of the first glycosaminoglycan. First layer further includes at least one therapeutic agent 335. It is envisioned that mesh 350 may provide additional strength to the implant for handling prior to implantation as well as for supporting tissue following implantation. Although first and second layers 320, 330, may appear as continuous layers across the entire mesh 350, in embodiments, any one of the layers of the multilayer implant may form a discontinuous layer on the other layers and/or the medical device, i.e., mesh.

Figure 5:
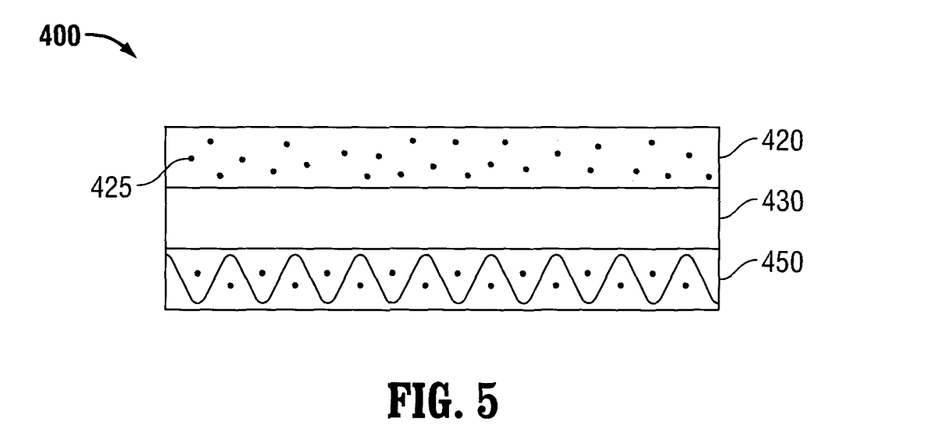
FIG. 5 is side view of a multilayer implant according to at least one embodiment described herein.

In addition, the medical device, i.e. the surgical mesh, may be positioned along any portion of the multilayer implants described herein. For example, in embodiments as shown in FIG. 5, mesh 450 is positioned along an outer surface of implant 400, which includes first layer 420 containing therapeutic agent 425 and second layer 430 positioned between at least a portion of mesh 450 and first layer 420. First layer 420 includes at least one glycosaminoglycan having a lower degree of acetylation (DA) than the at least one glycosaminoglycan of second layer 430. In such embodiments, second layer 430 may be in the form of a non-porous film and acting as a barrier for tissue ingrowth between tissue on the side nearest first layer 420 and the tissue on the opposite side nearest mesh 450. Since first layer 420 includes a glycosaminoglycan having a lower degree of acetylation (DA), first layer 420 may display a shorted in vivo persistence thereby degrading or being absorbed faster than second layer 430. In turn, the porosity of first layer 420, as well as the release of therapeutic agent 425, may increase thereby promoting tissue ingrowth in first layer 420. Such an implant may be suitable for positioning between tissues known to form adhesions. The implants described herein may also be suitable for hernia repair, repair of vaginal prolapse, and the like.

It will be understood that various modifications may be made to the embodiments disclosed herein. For example, the controlled release of a therapeutic agent may be influenced by modifying the degree of acetylation of chitosan in any one layer and/or adding any number of layers necessary to sustain or control the release of the therapeutic agent in a timely and therapeutically efficient manner. Therefore, the above description should not be construed as limiting, but merely as an exemplification of the embodiments. Those skilled in the art will envision other modifications within the scope and spirit of the present disclosure. Such modifications and variations are intended to come within the scope of the following claims.

What is claimed is:

1. A multilayer implant for delivery of a therapeutic agent comprising:
   a first non-porous film layer comprising a first glycosaminoglycan composition including a first chitosan having a first degree of acetylation, the first chitosan covalently bonded to a poly(ethylene glycol) functionalized to include pendant electrophilic groups,
   a second layer comprising a second glycosaminoglycan composition comprising at least one second chitosan having a second degree acetylation different than the first degree of acetylation wherein at least one of the first and second layers further comprises a therapeutic agent.

2. The implant of claim 1, wherein the first chitosan comprises a degree of acetylation of about 1% to about 10%.

3. The implant of claim 1, wherein the second chitosan comprises a degree of acetylation of about 10% to about 70%.

4. The implant of claim 1, wherein the therapeutic agent is selected from a group consisting of antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, enzymes and combinations thereof.

5. The implant of claim 1, wherein the therapeutic agent comprises an antimicrobial agent.

6. The implant of claim 1, further comprising a mesh.

7. The implant of claim 6, wherein the mesh is positioned between the first non-porous layer and the second layer.

8. The implant of claim 6, wherein the first non-porous layer is positioned between the mesh and the second layer.

9. The implant of claim 1, wherein
the second chitosan is bonded to a biocompatible polymer including pendant electrophilic groups.

10. The implant of claim 9 wherein the biocompatible polymer comprises a poly(ethylene glycol) functionalized to include pendant electrophilic groups.

11. The implant of claim 9 wherein the biocompatible polymer comprises electrophilic groups selected from a group consisting of N-hydroxysuccinimide ester (NHS), N-hydroxysulfosuccinimide ester (SNHS), N-hydroxyethoxylated succinimide ester (ENHS) and combinations thereof.

12. The implant of claim 9, wherein the first chitosan comprises a degree of acetylation of about 1% to about 10%.

13. The implant of claim 9, wherein the second chitosan comprises a degree of acetylation of about 10% to about 70%.

14. The implant of claim 1, wherein the first non-porous layer prevents tissue ingrowth.

15. The implant of claim 14, wherein the second layer comprises a porous scaffold for cellular attachment and/or tissue ingrowth.

16. The implant of claim 15, wherein the first non-porous film layer comprises an anti-adhesive agent and the second layer comprises a therapeutic agent which promotes tissue attachment or ingrowth.

17. The implant of claim 1 wherein the poly(ethylene glycol) comprises electrophilic groups selected from a group consisting of N-hydroxysuccinimide ester (NHS), N-hydroxysulfosuccinimide ester (SNHS), N-hydroxyethoxylated succinimide ester (ENHS) and combinations thereof.

18. A multilayer implant for delivery of a therapeutic agent comprising:
a first non-porous film layer comprising a first glycosaminoglycan composition including a first chitosan having a first degree of acetylation and a second chitosan having a second degree acetylation different than the first degree of acetylation, at least one of the first and second chitosans covalently bonded to a poly(ethylene glycol) functionalized to include pendant electrophilic groups
a second layer comprising a second glycosaminoglycan composition comprising a third glycosaminoglycan having a third degree acetylation and a fourth glycosaminoglycan having a fourth degree acetylation different than the third degree of acetylation wherein at least one of the first and second layers further comprises a therapeutic agent.

19. The implant of claim 18 wherein the second glycosaminoglycan composition comprises a glycosaminoglycan selected from a group consisting of hyaluronic acid, chondroitin, dermatan, chitin, chitosan, keratan, heparin, and derivatives and combinations thereof.

20. The implant of claim 18 wherein the first and second glycosaminoglycan compositions comprise the same glycosaminoglycan.

21. The implant of claim 18 wherein the first and second glycosaminoglycan compositions comprise different glycosaminoglycan.

22. The implant of claim 18, wherein the first chitosan includes a degree of acetylation of about 1% to about 10% and the second chitosan includes a degree of acetylation of about 10% to about 70%, wherein the first chitosan represents about 80% to about 95% of the first glycosaminoglycan composition and the second chitosan represents about 5% to about 20% of the first glycosaminoglycan composition.

23. The implant of claim 22, wherein the first chitosan includes a degree of acetylation of about 1% to about 2%.

* * * * *